(12) United States Patent
Becker et al.

(10) Patent No.: US 9,938,517 B2
(45) Date of Patent: Apr. 10, 2018

(54) SMALL ENZYME-CONTAINING GRANULES

(71) Applicant: DANISCO US INC., Palo Alto, CA (US)

(72) Inventors: Nathaniel T. Becker, Hillsborough, CA (US); Robert I. Christensen, Pinole, CA (US); Mark S. Gebert, Pacifica, CA (US); Antti Pekka Vaha-Vahe, Hanko (FI)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 15/490,552

(22) Filed: Apr. 18, 2017

(65) Prior Publication Data

US 2017/0283785 A1    Oct. 5, 2017

Related U.S. Application Data

(60) Continuation of application No. 14/679,263, filed on Apr. 6, 2015, now Pat. No. 9,657,284, which is a continuation of application No. 13/856,354, filed on Apr. 3, 2013, now abandoned, which is a division of application No. 12/867,172, filed as application No. PCT/US2009/033766 on Feb. 11, 2009, now abandoned.

(60) Provisional application No. 61/028,748, filed on Feb. 14, 2008, provisional application No. 61/115,146, filed on Nov. 17, 2008.

(51) Int. Cl.
| | |
|---|---|
| *C12N 11/14* | (2006.01) |
| *C12N 9/98* | (2006.01) |
| *C11D 3/386* | (2006.01) |
| *C11D 17/00* | (2006.01) |
| *A23K 20/189* | (2016.01) |
| *C12N 9/42* | (2006.01) |

(52) U.S. Cl.
CPC ............. *C12N 9/98* (2013.01); *A23K 20/189* (2016.05); *C11D 3/38645* (2013.01); *C11D 17/0039* (2013.01); *C12N 9/2437* (2013.01); *C12N 11/14* (2013.01); *C12Y 302/01004* (2013.01)

(58) Field of Classification Search
CPC ...................................................... C12N 11/14
See application file for complete search history.

(56) References Cited

U.S. PATENT DOCUMENTS

| | | | |
|---|---|---|---|
| 4,689,297 | A  | 8/1987 | Good et al. |
| 5,324,649 | A  | 6/1994 | Arnold et al. |
| 6,120,811 | A  | 9/2000 | Mahmood |
| 6,583,099 | B2 | 6/2003 | Christensen, Jr. |
| 6,602,841 | B1 | 8/2003 | Becker et al. |
| 6,933,141 | B1 | 8/2005 | Bach |
| 7,018,821 | B2 | 3/2006 | Becker et al. |

(Continued)

FOREIGN PATENT DOCUMENTS

| | | |
|---|---|---|
| WO | WO93/07263 | 4/1993 |
| WO | WO95/00121 | 1/1994 |

OTHER PUBLICATIONS

International Search Report dated May 25, 2009, for PCT Patent Application No. PCT/US2009/033766, filed on Feb. 11, 2009.

*Primary Examiner* — Rosanne Kosson

(57) ABSTRACT

The invention provides small enzyme-containing granules having an inorganic salt core and an enzyme-containing layer coated over the core, and methods for producing such granules. The majority of the enzyme granules are less than 300 µm in diameter. The granules are suitable for incorporation into compositions such as cleaning, textile processing, and animal feed compositions.

11 Claims, 1 Drawing Sheet

(56) References Cited

U.S. PATENT DOCUMENTS

| | | |
|---|---|---|
| 7,691,438 B2 | 4/2010 | Jacob et al. |
| 8,076,113 B2 | 12/2011 | Dale et al. |
| 2006/0073193 A1 | 4/2006 | Marcussen et al. |
| 2008/0031998 A1 | 2/2008 | Marcussen et al. |

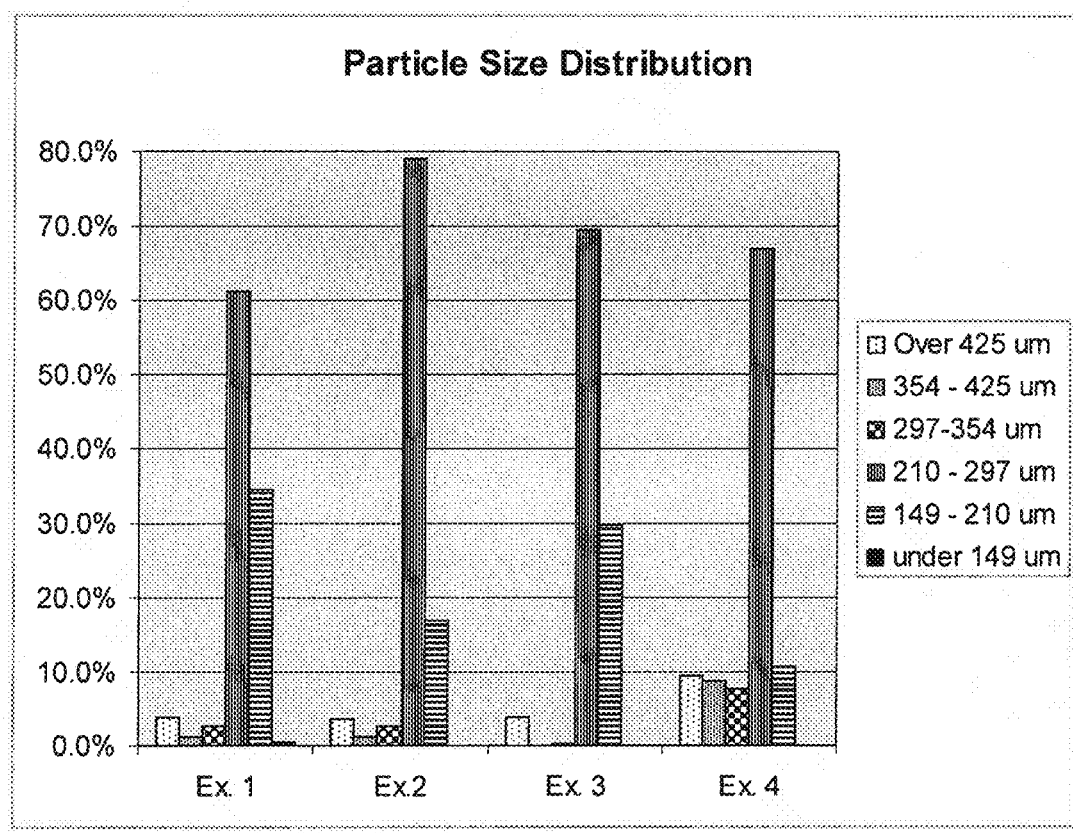

SMALL ENZYME-CONTAINING GRANULES

CROSS-REFERENCE TO RELATED APPLICATIONS

This application is a continuation of U.S. patent application Ser. No. 13/856,354, filed Apr. 3, 2013, which is a division of U.S. patent application Ser. No. 12/867,172, filed Nov. 22, 2010, which is the National Stage of International Application No. PCT/US2009/033766, filed Feb. 11, 2009, which claims the benefit of U.S. Provisional Application No. 61/028,748, filed Feb. 14, 2008, and U.S. Provisional Application No. 61/115,146, filed Nov. 17, 2008, both of which are incorporated by reference herein in their entireties.

FIELD OF THE INVENTION

The invention relates to small enzyme-containing granules produced in a fluidized bed spray coater, wherein the majority of the particles have a diameter of less than 300 microns and contain a single core.

BACKGROUND

Enzyme-containing granules are incorporated into products in several industries, including detergent, textile-processing, food (e.g., baking), animal feed, and fuel ethanol industries. Such granules may be prepared by a number of technologies, including fluidized bed spray coating, high sheer granulation, extrusion, spheronization, prilling, and spray drying.

Enzyme-containing granules of a small size (e.g., less than 300 micron diameter) are desirable in certain applications because small granules produce less dust and better protect enzymes against deactivating agents than do spray dried powders, while being easier to blend more homogeneously and inconspicuously with other powdered ingredients common in these industries. Such powders include surfactants and other detergent ingredients, buffers, salts, grain flours, starches, sugars, and/or inert diluents. A smaller granule has less tendency to segregate when blended into such powders and fine granular materials. Further, a given mass of smaller enzyme-containing granules will contain many more individual granules than the same mass of larger granules, and hence will provide greater homogeneity (less variation in net concentration) within a sample or aliquot of the powder into which it is blended, particularly for smaller sample sizes, e.g., less than about 50 to 100 grams of powder per aliquot. Granules with diameters in the range of 150 to 350 microns are advantageous because they are not so small that they produce large amounts of dust or are vulnerable to loss in enzyme potency and they are not so large that they blend poorly with typical powdered products.

It would be desirable to prepare such granules in a top-spray fluid bed coater because this technology can produce coated granules at a relatively low production cost and low equipment cost relative to its high productivity, i.e., mass of granules produced per unit time. With such a coating process, by judicious selection of the size distribution of the core particles, a resultant narrow and defined particle size distribution of final coated product can be achieved, which is advantageous for homogeneous quality and blending with powders.

A top-spray fluid bed coater is a coating vessel in which a bed of particles is suspended in a randomly circulating or churning bed produced by upward flow of air through a screen or retaining plate at the base of the vessel, and into which liquid coating solutions can be directed via spray nozzles inserted into the bed. Top-spray fluid bed coating is a well-established technology for producing coated enzyme-containing granules in a larger size range, i.e., where the majority of the granules have a diameter greater than 300 microns. However, with smaller granules, there is a strong tendency for the fluidized granules to agglomerate or stick together when sprayed with enzymes and other solutions, due to the presence of binders in the coating solutions. Agglomeration of fine powders is often employed deliberately to produce dry products, but such agglomerated powders are often undesirable because they typically have a broad particle size distribution, do not flow freely, and tend to form dusts or break down to fines when subjected to shear, impact, or other forces encountered in handling. Furthermore, coating of agglomerates is typically inefficient, since much of the coating material is incorporated into interstitial zones, rather than evenly coating the substrate particles.

There is a need for an improved method for production of small, uniformly coated, substantially discrete enzyme-containing granules in a top-spray fluid bed coating process.

BRIEF SUMMARY OF THE INVENTION

In one aspect, the invention provides a population of enzyme-containing granules. At least about 95% of the granules in the population contain a single core consisting of one or more inorganic salts, and the granules contain an enzyme-containing layer coated over the core. In some embodiments, at least about 50%, 60%, 70%, 80%, or 90% of the granules contain a diameter of about 150 to about 300 microns. In some embodiments, at least about 50%, 60%, 70%, 80%, or 90% of the granules contain a diameter of about 200 microns to about 350 microns. In some embodiments, at least about 50%, 60%, 70%, 80%, or 90% of the granules contain a diameter of about 150 to about 355 microns.

In one embodiment, the core consists of sodium sulfate. In some embodiments, at least about 80% or 90% of the cores contain a diameter of about 150 to about 250 microns. In some embodiments, at least about 80% or 90% of the cores contain a diameter of about 200 to about 300 microns. In some embodiments, the cores contain a bulk density greater than about 1.2 g/ml or 1.4 g/ml.

In some embodiments, the enzyme-containing layer contains an enzyme selected from a protease, a cellulase, an amylase, and a phytase. In some embodiments, the enzyme-containing layer further contains at least one of a polymer, a sugar, a starch, and a surfactant.

In some embodiments, the granules further contain a layer containing a barrier salt coated over the enzyme-containing layer. In one embodiment, the barrier salt layer contains sodium sulfate. In some embodiments, the barrier salt layer contains a mixture of two or more salts. In some embodiments, the barrier salt layer contains a mixture of two or more inorganic sulfate salts. In one embodiment, the barrier salt layer contains a mixture of sodium sulfate and magnesium sulfate.

In some embodiments, the granules further contain an outer coating layer containing a polymer coated over the barrier salt layer. The outer coating layer optionally further contains a pigment in addition to the polymer. In one embodiment, the polymer is a polyvinyl alcohol.

In some embodiments, the granules contain an outer coating layer containing a pigment coated over the barrier salt later.

In another aspect, the invention provides a composition containing a population of enzyme-containing granules as described above. In some embodiments, the composition is a detergent composition. In some embodiments, the composition is a textile processing composition. In some embodiments, the composition is an animal feed composition.

In another aspect, the invention provides a method of making enzyme-containing granules, including coating an enzyme-containing layer onto cores in a fluidized bed spray coater. At least about 95% of the granules produced by the method contain a single core consisting of one or more inorganic salts. In some embodiments, at least about 50%, 60%, 70%, 80%, or 90% of the granules produced by the method contain a diameter of about 150 to about 300 microns. In some embodiments, at least about 50%, 60%, 70%, 80%, or 90% of the granules produced by the method contain a diameter of about 200 to about 350 microns. In some embodiments, at least about 50%, 60%, 70%, 80%, or 90% of the granules contain a diameter of about 150 to about 355 microns.

In one embodiment of the method, the cores consist of sodium sulfate. In some embodiments, at least about 80% or 90% of the cores contain a diameter of about 150 to about 250 microns. In some embodiments, at least about 80% or 90% of the cores contain a diameter of about 200 to about 300 microns. In some embodiments, the cores contain a bulk density greater than about 1.2 g/ml. In some embodiments, the cores contain a bulk density greater than about 1.2 or 1.4 g/ml. In some embodiments, the cores are pre-sieved to a particle dispersity index of about 2.0 or less, 2.5 or less, or 3.0 or less.

In some embodiments, the method further includes coating a layer containing a barrier salt over the enzyme-containing layer, wherein the granules are not removed from the fluidized bed spray coater prior to addition of the barrier salt layer. In one embodiment, the barrier salt layer contains sodium sulfate. In some embodiments, the barrier salt layer contains a mixture of two or more salts. In some embodiments, the barrier salt layer contains a mixture of two or more inorganic sulfate salts. In one embodiment, the barrier salt layer contains a mixture of sodium sulfate and magnesium sulfate. In some embodiments, the method further includes coating an outer coating layer containing a polymer, and optionally further containing a pigment, over the barrier salt layer, wherein the granules are not removed from the fluidized bed spray coater prior to addition of the outer coating layer. In one embodiment, the polymer is a polyvinyl alcohol. In some embodiments, the method further includes coating an outer coating layer containing a pigment over the barrier salt later, wherein the granules are not removed from the fluidized bed spray coater prior to addition of the outer coating layer.

BRIEF DESCRIPTION OF THE DRAWINGS

FIG. 1 depicts particle size distribution for enzyme granules prepared as described in Examples 1-4.

DETAILED DESCRIPTION

The invention provides methods for the production of small coated, substantially discrete (i.e., substantially non-agglomerated) enzyme-containing granules in a top-spray fluidized bed coating process, and enzyme-containing granules produced by the methods.

Enzyme-containing granules as described herein may be used in applications such as cleaning (e.g., detergents), textile processing, food (e.g., baking), animal feed, and fuel ethanol production.

Enzyme-Containing Granules

The invention provides small enzyme-containing granules. A granule of the invention includes a single, discrete core and an enzyme-containing layer coated over the core. The core consists of one or more inorganic salts. In one embodiment, the core consists of sodium sulfate. The diameter of an enzyme granule of the invention is about 150 μm to about 300 μm, about 150 μm to about 350 μm, about 150 μm to about 355 μm, about 180 μm to about 300 μm, about 180 μm to about 350 μm, about 210 μm to about 350 μm, about 212 μm to about 355 μm, or about 180 μm to about 355 μm. In various embodiments, the diameter of an enzyme granule is any of about 150, 160, 170, 180, 190, 200, or 210 μm to any of about 250, 260, 270, 280, 290, 300, 310, 320, 330, 340, 350, or 355 μm. The diameters of the salt cores in the granules is about 100 μm to about 250 μm, about 150 μm to about 250 μm, or about 250 μm to about 300 μm. Enzyme-containing granules of the invention are produced in a fluid bed spray coater.

The enzyme layer contains one or more enzymes. The enzyme layer may also contain one or more of a polymer, a sugar, a starch, and a surfactant.

In some embodiments, an enzyme-containing granule includes a barrier layer coated over the enzyme layer to insulate or impede transport of water and inactivating substances to the enzyme and/or to improve mechanical strength and reduce friability of the granule. A barrier layer contains a salt (e.g., sodium sulfate), a polysaccharide (e.g., starch), a sugar (e.g., sucrose), or a combination thereof.

In some embodiments, an enzyme-containing granule includes an outer coating layer. The outer coating layer may be coated over the enzyme layer or may be coated over a barrier layer. An outer coating layer may serve any of a number of functions in an enzyme-containing granule, depending on the end use of the granule. For example, an outer coating may render the enzyme resistant to oxidation by bleach, bring about a desirable rate of dissolution upon introduction of the granule into an aqueous medium, provide a barrier against ambient moisture in order to enhance the storage stability of the enzyme, and/or improve mechanical stability and reduce tendency of the granule to break down and form dust. An outer coating layer may contain a polymer, for example, polyvinyl alcohol, and/or a pigment.

In some embodiments, the enzyme-containing granules contain about 50% to about 70% inorganic salt core (for example, sodium sulfate), about 1% to about 25% enzyme solids layer (for example, enzyme and one or more of sucrose, starch, surfactant, and polymer, about 10% to about 20% barrier layer (for example, a salt such as sodium sulfate or a mixture of two or more salts such as a mixture of sodium sulfate and magnesium sulfate) and/or about 5 to about 10% outer coating layer (for example, a layer containing polymer and/or pigment, such as polyvinyl alcohol, titanium dioxide, and surfactant, or polyvinyl alcohol and talc) by weight. In some embodiments, the granules contain enzyme in an amount that is about 0.5 to about 25% of the weight of the granule, for example, about 0.5, 1, 2, 5, 10, 15, 20, or 25% of the weight of the granule.

The invention also provides a population of enzyme-containing granules, with at least about 95%, 98%, or 99% of the granules in the population containing a single, discrete core consisting of one or more inorganic salts and an enzyme layer coated over the core. In a population of granules as described herein, at least about 50%, 60%, 70%, 80%, 85%, 90%, or 95% of the granules have a diameter of about 150 µm to about 300 µm, about 150 µm to about 350 µm, about 150 µm to about 355 µm, about 180 µm to about 300 µm, about 180 µm to about 350 µm, about 210 µm to about 350 µm, about 212 µm to about 355 µm, or about 180 µm to about 355 µm. In some embodiments, at least about 50%, 60%, 70%, 80%, 85%, 90%, or 95% of the granules have a diameter of any of about 150, 160, 170, 180, 190, 200, or 210 µm to any of about 250, 260, 270, 280, 290, 300, 310, 320, 330, 340, 350, or 355 µm.

In some embodiments, a population of enzyme-containing granules as described herein contains a particle size dispersity index of about 2.0 or less, about 2.5 or less, or about 3.0 or less. "Particle size dispersity index" ("PSDI") as used herein refers to the ratio of particle diameters of the $90^{th}$ weight-average percentile (D90) to the weight-average $10^{th}$ percentile (D10) in a sample. 10% by weight of the particles in the sample are greater than the D90 diameter and 10% by weight of the particles in the sample are less than the D10 diameter.

In some embodiments, the dust level generated by a population of granules as described herein, as measured by the Heubach test, is less than about 50, 40, 30, 20, 10, or 5 mg/pad.

Salt Core

The core of an enzyme-containing granule as described herein consists of one or more inorganic salts. In some embodiments, the core consists of sodium sulfate, sodium citrate, sodium chloride, calcium sulfate, or a combination thereof. In one embodiment, the core consists of sodium sulfate.

The salt core of an enzyme-containing granule as described herein has a diameter of about 100 µm to about 250 µm, about 150 µm to about 250 µm, or about 250 µm to about 300 µm.

In some embodiments, prior to preparation of a population of enzyme-containing granules, salt cores are pre-sieved to a particle size dispersity index of about 2.0 or less, about 2.5 or less, or about 3.0 or less. Pre-sieving may be performed using methods known in the art, for example, using a vibratory sieve shaker or pneumatic classifier. For example, cores may be pre-sieved, by conventional sieving through a 250 µm sieve, collecting the fraction from above the 150 µm sieve, and discarding or recycling fines that pass through the 150 µm sieve. Pre-sieving may also be performed in a fluid bed coater by blowing the fines out with the air flow. The air flow can be adjusted so that the desired core size will be retained.

Typically, the salt core has a bulk density greater than about 1.0 g/ml. In some embodiments, the bulk density is greater than 1.2 g/ml. In some embodiments, the bulk density is greater than about 1.4 g/ml. In some embodiments, the bulk density is any of about 1.0, 1.2, or 1.4 g/ml to any of about 1.6, 1.7 or 1.8 g/ml. Bulk density may be measured as "poured bulk density" or "non-tapped bulk density" by filling a graduated cylinder with a known volume of particles, measuring the mass of the particles in the cylinder, and calculating bulk density by dividing the mass by the volume.

Enzyme Layer

A single enzyme or a combination of two or more enzymes may be included in the enzyme layer of granules as described herein. In some embodiments, the enzyme layer includes an enzyme that is capable of hydrolyzing a substrate, e.g., a stain. Such an enzyme is typically a hydrolase, for example, a protease (bacterial (e.g., a subtilisin) or fungal; acid, neutral, or alkaline), an amylase (alpha or beta), a lipase, or a cellulase. In some embodiments, the enzyme is a subtilisin, for example, as described in U.S. Pat. No. 4,760,025, EP Patent No. 130 756, or PCT Application No. WO 91/06637. In some embodiments, the enzyme is a cellulase, for example, Multifect L250™ or Puradax™, commercially available from Danisco US, Inc., Genencor Division. In some embodiments, the enzyme layer includes an oxidase, an oxygenase, a transferase, a dehydratase, a reductase, a hemicellulase, a peroxidase, a phospholipase, an esterase, a cutinase, a pectinase, a keratinase, a lipoxygenase, a ligninase, a pullulanase, a tannase, a pentosanase, a malanase, a β-glucanase, an arabinosidase, a hyaluronidase, a chondroitinase, a laccase, a catalase, an isomerase, a pectate lyase, or a mannanase, or a combination thereof. In some embodiments, the enzyme layer includes a phytase. In some embodiments, the enzyme layer includes a perhydrolase enzyme, such as, for example, an enzyme as described in PCT Application No. WO 05/056782. In some embodiments, the enzyme layer includes one or more enzymes sold under the trade names Purafect™, Purastar™ Properase™, Puradax™, Clarase™, Multifect™, Maxacal™, Maxapem™, and Maxamyl™ by Danisco US, Inc, Genencor Division. (see U.S. Pat. No. 4,760,025 and PCT Application No. WO 91/06637); Alcalase™, Savinase™, Primase™, Durazyme™, Duramyl™, Ovozyme™ Polarzyme™, and Termamyl™ sold by Novo Industries A/S (Denmark).

The enzyme layer may also optionally include one or more other components in addition to the enzyme(s). Such non-enzyme components include, but are not limited to, polymers (e.g., polyvinyl alcohol, polyethylene glycol), sugars (e.g., sucrose, saccharose, glucose, fructose, galactose, maltodextrin), starches (e.g., corn starch, wheat starch, tapioca starch, potato starch, chemically or physically modified starch), dextrins, antifoam agents (e.g., polyether polyols such as Foamblast 882 (Emerald Foam Control), Erol DF 204K (Ouvrie PMC), DG436 (ODG Industries, Inc.), KFO 880 (KABO Chemicals, Inc.)), sugar alcohols (e.g., sorbitol, maltitol, lactitol, xylitol), surfactants (e.g., alcohol ethoxylates such as Neodol 23-6.5 (Shell Chemical LP, Houston, Tex.) and Lutensol TO65 (BASF)), and anti-redeposition agents (e.g., polyethylene glycol polyesters such as Repel-o-Tex SRP6 (Rhodia, Inc.), Texcare SRN-100 or SRN-170 (Clariant GmbH, Sorez-100 (ISP Corp.)).

An "antifoam agent" is a compound that is used to prevent or break foam. These can also be referred to as defoamers, or defoaming agents. These compounds are surface active substances which decrease the surface elasticity of liquids and prevent metastable foam formation. The foam breaks as a result of the tendency to attain the equilibrium between the surface elasticity of the liquid and the surface active substances. (Vardar-Sukan (1991) *Recent Adv. Biotechnol.* 113-146) Antifoams useful in the granules described herein are generally suitable for use in a bioprocess. Suitable antifoam agents include, but are not limited to, fats, oils, waxes, aliphatic acids or esters, alcohols, sulfates, sulfonates, fatty acids, soaps, nitrogenous compounds, phosphates, polyglycols, sulfides, thio compounds, siloxanes and halogenated and inorganic compounds. (Ghildyal (1988) *Adv. Appl. Microbiol.* (1988) 33:173-222). In some embodiments, oils, fatty acids, esters, polyglycols and siloxanes are useful. In some embodiments, the antifoam agent is ethylene oxide propylene oxide copolymer. In one embodiment, the ethylene oxide propylene oxide copolymer has an approximate molecular weight of 2200 (e.g., available as Mazu™ from Mazer Chemicals, Inc.).

Barrier Layer

In some embodiments, a barrier layer is coated over the enzyme layer in an enzyme-containing granule as described herein. In some embodiments, the barrier layer contains one or more salts, for example, sodium sulfate, sodium citrate, magnesium sulfate, potassium sulfate, and/or ammonium sulfate. In some embodiments, the barrier layer comprises, consists of, or consists essentially of sodium sulfate. In some embodiments, the barrier layer comprises, consists of, or consists essentially of a mixture of sodium sulfate and magnesium sulfate. In some embodiments, the barrier layer contains a sugar (e.g., sucrose), a polysaccharide (e.g., starch), or a combination thereof.

In some embodiments, the barrier layer contains a mono-, di-, or trivalent water soluble inorganic sulfate salt, e.g., sodium, potassium, ammonium, magnesium, aluminum, ferrous, and/or ferric sulfate salt(s) or a mixture of two or more soluble inorganic sulfate salts.

In some embodiments, the barrier layer is a mixture of two salts with one salt present at any of at least about 50%, 60%, 70%, 80%, or 90% by weight relative to the total weight of the barrier layer. In some embodiments, the two salts are present in a ratio of about 50:50, 55:45, 60:40, 65:35, or 70:30 by weight of the barrier layer. In one embodiment, the mixture of two salts is a mixture of sodium sulfate and magnesium sulfate. In some embodiments, the barrier layer consists of sodium sulfate and magnesium sulfate in a ratio of about 30:70 to about 70:30 by weight of the barrier layer, for example, 30:70, 35:65, 40:60, 45:55, 50:50, 55:45, 60:40, 65:35, or 70:30.

In some embodiments, the barrier layer is hydrated. The term "hydrated" means that the barrier material contains water in a free or bound form, or a combination of the two. The water of hydration can be added either during or after the coating process. The degree of hydration will be a function of the material itself and the temperature, humidity and drying conditions under which it is applied.

"Moderate or high" water activity means having a water activity of at least about 0.25, 0.30, or 0.35. The water activity referred to herein is that of the granule itself once it has the barrier material-but no further coatings-coated onto it. Further coatings may mask accurate measurement of the water activity of the barrier material as a distinct layer.

Without wishing to be bound by theory, it is expected that materials with a water activity greater than 0.25 will have a reduced driving force for picking up water under storage conditions in which the relative humidity is greater than 25%. Most climates have relative humidities above 25%. Many detergents have water activities in the range of about 0.3 to 0.4. If the water activity of the granule is actually higher than that of the surrounding detergent or storage climate, the driving force for pick up of water by the granule should be eliminated, and in fact water may be given up by the granule to its surroundings. Even if the water activity of the granule is lower than that of the detergent or the corresponding relative humidity, the water present in the barrier layer would act as a shield limiting the amount of water being picked up by the granule and affecting the protein core.

In the case of salt hydrates, the hydrated material is a crystalline salt hydrate with bound waters of crystallization. The hydrate should be chosen and applied in a manner such that the resulting coated granule will have a water activity in excess of 0.25, or as high as possible while still retaining a granule which is dry to the touch. By applying a salt hydrate, or any other suitable hydrated barrier material, in such a manner, one eliminates any driving force for further uptake of water by the granule. As an important consequence, the driving force for transport of substances which may be detrimental to enzyme activity, such as perborate or peroxide anion, is removed. Without water as a vehicle, these substances are less likely to penetrate the enzyme core. Empirical data demonstrates that enzyme activity in the granule is substantially enhanced by coating the enzyme core with stable salt hydrates.

Examples of suitable salts for production of a hydrated barrier layer include magnesium sulfate heptahydrate, zinc sulfate heptahydrate, copper sulfate pentahydrate, sodium phosphate dibasic heptahydrate, magnesium nitrate hexahydrate, sodium borate decahydrate, sodium citrate dihydrate and magnesium acetate tetrahydrate.

Outer Coating Layer

In some embodiments, an enzyme containing granule comprises an outer coating layer. In one embodiment, the outer coating layer is coated over the enzyme layer. In another embodiment, the outer coating layer is coated over a barrier layer, which is coated over the enzyme layer.

In some embodiments, the outer coating layer includes one or more polymers. Suitable polymers include, but are not limited to, polyvinyl alcohol (PVA), polyvinyl pyrrolidone (PVP), polyvinyl acetate, PVA-methylmethacrylate copolymer, PVP-PVA copolymer, cellulose derivatives such as methylcellulose, hydroxypropylmethyl cellulose, hydroxycellulose, ethylcellulose, caboxymethyl cellulose, hydroxypropyl cellulose, polyethylene glycol, polyethylene oxide, chitosan, gum arabic, xanthan, carrageenan, latex polymers, and enteric polymer.

In some embodiments, the outer coating layer includes PVA. Suitable PVAs for incorporation in the outer coating layer include partially hydrolyzed, fully hydrolyzed, and intermediately hydrolyzed PVAs having low to high degrees of viscosity. (See, e.g., U.S. Pat. No. 5,324,649.) In one embodiment, the outer coating layer includes partially hydrolyzed PVA having low viscosity.

In some embodiments, the outer coating layer includes one or more pigments. Nonlimiting examples of suitable pigments include finely divided whiteners, such as titanium dioxide or calcium carbonate, calcium sulfate, talc, or colored pigments or dyes. Typically, such pigments are low residue pigments upon dissolution. In addition to polymers and/or pigments, the outer coating layer may also include one or more of plasticizers, extenders, lubricants, surfactants, and anti-redeposition agents.

Suitable plasticizers include, but are not limited to, polyols (e.g., sugars, sugar alcohols, polyethylene glycols (PEGs), glycol, propylene glycol), urea, triethyl citrate, dibutyl or dimethyl phthalate, or water.

Suitable extenders include, but are not limited to, sugars (e.g., sucrose or starch hydrolysates, such as maltodextrin or corn syrup solids), clays (e.g., kaolin or bentonite), and talc. An "extender" is a substance (generally lower cost) added to another substance (generally higher cost and higher performance) to modify or dilute it.

Suitable lubricants include, but are not limited to, nonionic surfactants (e.g., Neodol, Lutensol TO 65), tallow alcohols, fatty acids, fatty acid salts (e.g., magnesium stearate), and fatty acid esters.

Suitable surfactants include, but are not limited to, alcohol ethoxylates such as Neodol 23-6.5 and Lutensol TO65.

Suitable anti-redeposition agents include, but are not limited to, polyethylene glycol polyesters such as Repel-o-Tex SRP6, Texcare SRN-100 or SRN-170, and Sorex-100.

Methods of Making Enzyme Granules

The invention provides methods for producing enzyme-containing granules as described above, with high coating efficiency and minimal agglomeration. The methods comprise coating an enzyme-containing layer onto inorganic salt cores in a fluidized bed spray coater. Optionally, the method also comprises coating a barrier layer onto the enzyme-containing layer, coating an outer coating layer onto the enzyme-containing layer, or coating a barrier layer onto the enzyme-containing layer and an outer coating layer onto the barrier layer, in the fluidized bed spray coater. At least about 95%, 98%, or 99% of the enzyme-containing granules produced in accordance with the methods described herein contain a single, discrete core (i.e., are not agglomerated and contain a ratio of granule to core of 1:1). In one embodiment, the inorganic salt cores consist of sodium sulfate.

In methods of the invention, the particle size distribution, shape, and density of the salt cores are controlled, permitting production of small, substantially discrete, coated granules. In some embodiments, this is achieved by pre-selecting or pre-sieving the initial charge of cores to a PSDI of about 2.0 or less, about 2.5 or less, or about 3.0 or less, prior to introduction into the fluidized bed spray coater. The salt cores comprise a bulk density greater than about 1.0, 1.2, or 1.4 g/ml, which results in more controlled fluidization and coating efficiency in the top-spray coater than salt cores with a lower bulk density. These factors of controlled size distribution and bulk density of the salt cores result in a controlled fluidization pattern with sufficient expansion of the bed (to avoid agglomeration), but minimization of physical elutriation (loss of particles into filters, scrubbers, or the exit air stream). In some embodiments, the air flow, spray rate, bed temperature, and/or atomization air pressure of the fluid bed coater are adjusted to substantially prevent agglomeration.

The enzyme-containing granules may be prepared in a continuous or discontinuous process. In a continuous process, the enzyme layer and barrier and/or outer coating layers are coated over the salt core without removal of the granules from the spray coater. In a discontinuous process, the granules are removed from the spray coater and re-introduced into a spray coater prior to addition of a barrier and/or outer coating layer.

A continuous process as described herein has the advantage of permitting preparation of discrete small enzyme granules within a single efficient operation of a fluid bed coater, requiring no separate preparation of enzyme particles before the coating step, or removal of unfinished product from the coater for addition of further coating layers in a subsequent operation. By eliminating the need to transfer uncoated enzyme cores between operations, this single contained process eliminates downtime and transfer losses, and minimizes the exposure of operators in the manufacturing plant to unsafe levels of airborn enzyme dusts and aerosols.

At least about 50%, 60%, 70%, 80%, 85%, 90%, or 95% of the granules produced in the methods described herein have a diameter of about of about 150 µm to about 300 µm, about 150 µm to about 350 µm, about 150 to about 355 µm, about 180 µm to about 300 µm, about 180 µm to about 350 µm, about 210 µm to about 350 µm, about 212 µm to about 355 µm, or about 180 µm to about 355 µm. In some embodiments, at least about 50%, 60%, 70%, 80%, 85%, 90%, or 95% of the granules have a diameter of any of about 150, 160, 170, 180, 190, 200, or 210 µm to any of about 250, 260, 270, 280, 290, 300, 310, 320, 330, 340, 350, or 355 µm.

In some embodiments, a population of enzyme-containing granules produced by a method as described herein contains a particle size dispersity index of about 2.0 or less, about 2.5 or less, or about 3.0 or less.

Compositions

The invention provides compositions containing enzyme-containing granules as described above. In addition to the enzyme-containing granules, the compositions contain components suitable for use of the granules in particular applications, such as cleaning (e.g., detergents), textiles, or animal feed.

Cleaning Compositions

In some embodiments, enzyme-containing granules as described herein are incorporated into a cleaning composition, such as a detergent, e.g., for laundry or dishwashing use, to provide cleaning performance and/or cleaning benefits. Enzymes suitable for inclusion in a cleaning composition include, but are not limited to, hemicellulases, peroxidases, proteases, cellulases, xylanases, lipases, phospholipases, esterases, cutinases, pectinases, keratinases, reductases, oxidases, phenoloxidases, lipoxygenases, ligninases, pullulanases, tannases, pentosanases, malanases, β-glucanases, arabinosidases, hyaluronidase, chondroitinase, laccases, perhydrolases, and amylases, or mixtures thereof. A typical combination is a cocktail of conventional applicable enzymes like protease, lipase, cutinase and/or cellulase in conjunction with amylase.

Adjunct materials may also be included in the cleaning composition, for example, to assist or enhance cleaning performance, for treatment of the substrate to be cleaned, or to modify the aesthetics of the cleaning composition as is the case with perfumes, colorants, dyes or the like. It is understood that such adjuncts are in addition to the enzyme-containing granules as described herein. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, enzyme stabilizers, catalytic materials, bleach activators, bleach boosters, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are described in U.S. Pat. Nos. 5,576,282, 6,306,812, and 6,326,348.

Surfactants—A cleaning composition as described herein may comprise a surfactant or surfactant system wherein the surfactant can be selected from nonionic surfactants, anionic surfactants, cationic surfactants, ampholytic surfactants, zwitterionic surfactants, semi-polar nonionic surfactants, and mixtures thereof. A surfactant is typically present at a level of about 0.1% to about 60%, about 1% to about 50% or about 5% to about 40% by weight of the subject cleaning composition.

Builders—A cleaning composition as described herein may comprise one or more detergent builder or builder system. When a builder is used, the subject cleaning composition will typically comprise at least about 1%, about 3% to about 60%, or about 5% to about 40% builder by weight of the subject cleaning composition.

Builders include, but are not limited to, the alkali metal, ammonium and alkanolammonium salts of polyphosphates, alkali metal silicates, alkaline earth and alkali metal carbonates, aluminosilicate builders, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof.

Chelating Agents—A cleaning composition as described herein may contain one or more chelating agent. Suitable chelating agents include, but are not limited to, copper, iron and/or manganese chelating agents and mixtures thereof. When a chelating agent is used, the cleaning composition may comprise about 0.1% to about 15%, or about 3.0% to about 10% chelating agent by weight of the subject cleaning composition.

Deposition Aids—A cleaning composition as described herein may contain one or more deposition aid. Suitable deposition aids include, but are not limited to, polyethylene glycol, polypropylene glycol, polycarboxylate, soil release polymers such as polytelephthalic acid, and clays such as Kaolinite, montmorillonite, atapulgite, illite, bentonite, halloysite, and mixtures thereof.

Dye Transfer Inhibiting Agents—A cleaning composition as described herein may include one or more dye transfer inhibiting agent. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones, and polyvinylimidazoles, and mixtures thereof. When present in a subject cleaning composition, dye transfer inhibiting agent may be present at levels of about 0.0001% to about 10%, about 0.01% to about 5%, or about 0.1% to about 3% by weight of the cleaning composition.

Dispersants—A cleaning composition as described herein may contain one or more dispersant. Suitable water-soluble organic dispersants include, but are not limited to, the homo- or co-polymeric acids or their salts, in which the polycarboxylic acid comprises at least two carboxyl radicals separated from each other by not more than two carbon atoms.

Enzyme Stabilizers—Enzymes for use in detergents can be stabilized by various techniques. Enzymes employed herein can be stabilized, for example, by the presence of water-soluble sources of calcium and/or magnesium ions in the finished compositions that provide such ions to the enzymes.

Catalytic Metal Complexes—A cleaning composition as described herein may include one or more catalytic metal complex. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243. Manganese-containing catalysts useful herein are known, and are described, for example, in U.S. Pat. No. 5,576,282. Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936 and 5,595,967.

Compositions herein may also include a transition metal complex of a macropolycyclic rigid ligand—abbreviated as "MRL". As a practical matter, and not by way of limitation, the compositions and cleaning processes herein can be adjusted to provide on the order of at least one part per hundred million of the active MRL species in the aqueous washing medium, and will often provide about 0.005 ppm to about 25 ppm, about 0.05 ppm to about 10 ppm, or about 0.1 ppm to about 5 ppm, of the MRL in the wash liquor. Suitable transition-metals in a transition-metal bleach catalyst include manganese, iron and chromium. In one embodiment, an MRL is an ultra-rigid ligand that is cross-bridged, such as 5,12-diethyl-1,5,8,12-tetraazabicyclo[6.6.2]hexadecane.

Suitable transition metal MRLs are readily prepared by known procedures, such as taught for example in PCT Application No. WO 00/332601 and U.S. Pat. No. 6,225,464.

The cleaning compositions disclosed herein of can be used to clean a situs on a surface or fabric. Typically at least a portion of the situs is contacted with a cleaning composition as described above, in neat form or diluted in a wash liquor, and then the situs is optionally washed and/or rinsed. Washing includes, but is not limited to, scrubbing, and mechanical agitation. A fabric may comprise most any fabric capable of being laundered in normal consumer use conditions. The disclosed cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

Textile Processing Compositions

In some embodiments, enzyme-containing granules as described herein are incorporated into a textile processing composition. Enzymes suitable for inclusion in a textile processing composition include, but are not limited to, cellulases, perhydrolases, polyesterases, amylases, phenol oxidizing enzymes (e.g., laccases), and catalases. In some embodiments, a textile processing composition may also include an anti-redeposition agent (e.g., Repel-O-Tex, Sorez 100 (ISP Corp.).

Animal Feed Compositions

In some embodiments, enzyme-containing granules as described herein are incorporated into an animal feed composition. Enzymes suitable for inclusion in a feed composition include cellulolytic and/or hemicellulolytic enzymes. Nonlimiting examples of enzymes suitable for incorporation into a feed composition include phytases, xylanases, phosphatases, proteases, amylases, esterases, redox enzymes, lipases, transferases, cellulases, phospholipases, ligninases, and β-glucanases.

The following examples are intended to illustrate, but not limit, the invention.

EXAMPLES

Example 1

2296 grams of sodium sulfate crystals, with a particle diameter size range of 150 μm to 250 μm, was loaded into a Vector FL-1 fluid bed coater and fluidized. To this, 5557 grams of a solution containing 23,608 U/ml of active neutral cellulase, 3.6% Sorez-100 from ISP Corp. (an anti-redeposition agent), and 0.36% polyvinyl alcohol (5/88 from Erkol) was spray-coated onto the sodium sulfate crystals.

The spray coating parameters were as follows:

| | |
|---|---|
| Solution Spray Rate | 6.5 gpm (grams per minute), increasing to 15.4 gpm over 2.5 hours. Kept at 15.4 gpm for remainder of experiment. |
| Inlet Temperature | 85° C., increased to 90° C. after 1 hour |
| Outlet temperature | Between 42° C. and 46° C. |
| Fluidization Air Flow | 50 cfm (cubic feet per minute) |
| Atomization Air Pressure | 40 pounds per square inch (psi), increasing to 50 psi over 2.5 hours. |

3017 grams of product was harvested, of which 2899 grams passed through a 40 mesh sieve (425 μm). The particle size distribution is shown in Table 1 and in FIG. 1.

TABLE 1

Particle Size Analysis for Enzyme Granules Produced in Example 1

| Particle size (μm) | Amount of particles (%) |
|---|---|
| Over 425 | 3.8 |
| 354-425 | 1.1 |
| 297-354 | 2.6 |
| 210-297 | 59.0 |
| 149-210 | 34.5 |
| Under 149 | 0.4 |

Example 2

1395 grams of the enzyme granules produced in Example 1 were loaded into a Vector FL-1 fluid bed coater and fluidized. 861 grams of an aqueous solution containing 172 grams of sodium sulfate were then spray coated onto the enzyme granules.

The spray coating parameters were as follows:

| | |
|---|---|
| Solution Spray Rate | 14.9 gpm |
| Inlet Temperature | 90° C. |
| Outlet temperature | Between 42° C. and 46° C. |
| Fluidization Air Flow | 53 cfm |
| Atomization Air Pressure | 40 psi |

1483 grams of final product was harvested. The particle size distribution is shown in Table 2 and in FIG. 1.

TABLE 2

Particle Size Analysis for Enzyme Granules Produced in Example 2

| Particle size (μm) | Amount of particles (%) |
|---|---|
| Over 425 | 3.8 |
| 354-425 | 0.0 |
| 297-354 | 0.3 |
| 210-297 | 67.1 |
| 149-210 | 28.7 |
| Under 149 | 0.1 |

Example 3

1395 grams of the enzyme granules produced in Example 2 were loaded into a Vector FL-1 fluid bed coater and fluidized. 861 grams of an aqueous solution containing 52 grams of PVA (Erkol 5/88), 112 grams of talc (Nytal 400), and 8.6 grams of Neodol 23/6.5 were then spray coated onto the enzyme granules.

The spray coating parameters were as follows:

| | |
|---|---|
| Solution Spray Rate | 10.8 gpm |
| Inlet Temperature | 95° C. |
| Outlet temperature | Between 49° C. and 50° C. |
| Fluidization Air Flow | 50 cfm |
| Atomization Air Pressure | 46 psi |

1477 grams of final product was harvested. The particle size distribution is shown in Table 3 and in FIG. 1.

TABLE 3

Particle Size Analysis for Enzyme Granules Produced in Example 3

| Particle size (μm) | Amount of particles (%) |
|---|---|
| Over 425 | 9.2 |
| 354-425 | 8.6 |
| 297-354 | 7.4 |
| 210-297 | 64.5 |
| 149-210 | 10.4 |
| Under 149 | 0.0 |

Example 4

2820 grams of unsifted sodium sulfate crystals (from Urumqi Huagao Trade Co., Ltd., Urumqi City, China ("Hanhua Grade C")) were loaded into a Vector FL-1 fluid bed coater and air sifted, i.e., fluidized for 30 minutes. Unsifted Hanhua Grade C sodium sulfate crystals had the following particle size distribution:

| Screen (μm) | Max % | Min % |
|---|---|---|
| 355 | 0 | 0 |
| 280 | 0 | 0 |
| 250 | 25 | 5 |
| 200 | 43 | 22 |
| 150 | 89 | 80 |

After the fluidization, 2660 grams of sodium sulfate crystals remained.

2287 grams of the air sifted sodium sulfate crystals were loaded into a Vector GL-1 fluid bed coater and fluidized. 5670 grams of a solution containing 23,608 U/ml of active neutral cellulase, 3.6% Sorez-100 ISP Corp.), and 0.36% polyvinyl alcohol (5/88 from Erkol) was spray-coated onto the sodium sulfate crystals.

The spray coating parameters were as follows:
Air-Sifting of Sulfate Crystals

| | |
|---|---|
| Inlet Temperature | 85° C. |
| Fluidization Air Flow | 52 cfm |
| Atomization Air Pressure | 20 psi |

Enzyme Solution Spray Coating

| | |
|---|---|
| Solution Spray Rate | 7.2 gpm, increasing to 15.5 gpm over 2.5 hours. Kept at 15.5 gpm for remainder of experiment. |
| Inlet Temperature | 85° C. |
| Outlet temperature | Between 39° C. and 48° C. |

-continued

| | |
|---|---|
| Fluidization Air Flow | 50 cfm |
| Atomization Air Pressure | 40 psi |

3057 grams of product was harvested, of which 2952 grams passed through a 40 mesh sieve.

The particle size distribution is shown in Table 4 and in FIG. 1.

TABLE 4

Particle Size Analysis for Enzyme Granules Produced in Example 4

| Particle size (μm) | Amount of particles (%) |
|---|---|
| Over 425 | 3.4 |
| 354-425 | 1.2 |
| 297-354 | 2.5 |
| 210-297 | 76.4 |
| 149-210 | 16.4 |
| Under 149 | 0.1 |

Example 5

149 kg of sodium sulfate crystals (Hanhua Grade C, particle size distribution described in Example 4), with a size range of 150 μm to 250 μm, was loaded into a pilot fluid bed coater with a bowl volume of approximately 93 liters and three spray nozzles and fluidized. 66 kg of a mixture of EG3 cellulase (216 U/g), sucrose (2.6 kg), and wheat starch (2.6 kg) was spray-coated onto the sodium sulfate crystals. 120 kg of sodium sulfate solution (25% in water) was then sprayed onto the enzyme containing layer.

The spray coating parameters were as follows:
Warm-up:

| | |
|---|---|
| Inlet Air Temperature | 70° C. |
| Fluidization Air Flow | 1175 Nm³/h (nominal or norm m³ of air per hour) |
| Atomization Air Pressure | 5.5 bar |

Enzyme Solution Spray Coating:

| | |
|---|---|
| Solution Spray Rate | 18.0 l/h for 20 minutes, then increasing to 33.0 l/h over 110 minutes. Kept at 33.0 l/h for remainder of the experiment. |
| Bed Temperature | 50° C. |
| Fluidization Air Flow | 1300 Nm³/h, then increasing to 1325 Nm³/h over 75 minutes |
| Atomization Air Pressure | 5.5 bar |

Sulfate Solution Spray Coating:

| | |
|---|---|
| Solution Spray Rate | 36 l/h, then increasing to 51 l/h over 35 minutes. Kept at 51 l/h for remainder of the experiment. |
| Bed Temperature | 52° C. |
| Fluidization Air Flow | 1325 Nm³/h, then increasing to 1375 Nm³/h over 60 minutes |
| Atomization Air Pressure | 4.0 bar |

145 kg of granules were harvested, of which 94% were smaller than 300 μm and 59% were smaller than 250 μm. The particle size distribution is shown in Table 5.

TABLE 5

Particle Size Analysis for Enzyme Granules Produced in Example 5

| Particle size (μm) | Amount of particles (%) |
|---|---|
| Over 355 | 1.1 |
| 300-355 | 4.9 |
| 250-300 | 34 |
| 212-250 | 51 |
| 180-212 | 9.2 |
| Under 150 | 0 |

Example 6

3156 kg of sodium sulfate crystals (Hanhua Grade C, particle size distribution described in Example 4), with a size range of 150 μm to 250 μm, was loaded into a top spray fluid bed coater with a 5.6 m³ bowl and fluidized. 8681 kg of a mixture of neutral cellulase (19062 U/g), polyvinyl alcohol (Celvol E 5/88 from Celanese; 204 kg of 10% solution in water) and Repel-o-Tex (block copolymer of polyethylene glycol and polyester, from Rhodia; 670 kg of 21% suspension in water) was spray-coated onto the sodium sulfate crystals. 1462 kg of sodium sulfate solution (25% in water) was sprayed onto the enzyme containing layer.

The spray coating parameters were as follows:
Warm-up:

| | |
|---|---|
| Inlet Air Temperature | 80° C. |
| Fluidization Air Flow | 23000 Nm³/h |
| Atomization Air Pressure | 5.0 bar |

Enzyme Solution Spray Coating:

| | |
|---|---|
| Solution Spray Rate | 420 l/h for 20 minutes, then increasing to 910 l/h over 2 hours. Kept at 910 l/h for remainder of the experiment. |
| Bed Temperature | 45-48° C. |
| Fluidization Air Flow | 23000 Nm³/h |
| Atomization Air Pressure | 5.0 bar |

Sulfate Solution Spray Coating:

| | |
|---|---|
| Solution Spray Rate | 896 l/h for 5 minutes, then increasing to 1120 l/h over 25 minutes. Kept at 1120 l/h for remainder of the experiment. |
| Bed Temperature | 45° C. |
| Fluidization Air Flow | 23000 Nm³/h |
| Atomization Air Pressure | 3.5 bar |

2950 kg of granules were harvested through a 355 μm sieve. The final product smaller than 355 μm in diameter had 88% of particles smaller than 300 μm, 1.0% smaller than 212 μm, 0.02% smaller than 180 μm, and none below 150 μm. The mean particle size was 276 μm.

Example 7

Small Neutral Cellulase Based Granules Made at Laboratory Scale

1. Preparation of Enzyme Granules ("Enzyme Coated Cores")

5,008 grams of Indiage XL neutral cellulase concentrate was mixed with 953 grams of Repel-O-Tex SRP6, which had been previously dissolved in water at 60° C. at a concentration of 19.7%, and 139 grams of PVA (Erkomat), which had been previously dissolved in water at 80° C. at a concentration of 13.5%. This enzyme/polymer mixture was sprayed onto 2,286 grams of Hanhua Grade C sodium sulfate seeds with a size range of 150 µm to 250 µm in a Vector FL-1 fluid bed coater using the following coating parameters:

| | |
|---|---|
| Seed Charge | 2286 grams |
| Enzyme Feed Rate | 9-17 grams/minute |
| Atomization Pressure | 40-46 psi |
| Inlet Temperature | 80-95° C. |
| Outlet Temperature | 40-43° C. |
| Airflow | 50-53 cfm |

After coating the sodium sulfate seeds with enzyme, enzyme coated cores were removed from the coater and weighed to determine an overall enzyme mass yield. They were also sieved through a 425 micron sieve to determine mass yield of granules <425 microns. The enzyme mass yield and yield of granules below 425 micron were as follows:

| | |
|---|---|
| Enzyme Mass Yield: | 92.15% |
| <425 microns | 94.46% |
| >425 microns (overs) | 5.54% |

The particle size distribution is shown in Table 6.

TABLE 6

Particle Size Analysis for Enzyme Granules Produced in Example 7.1

| Particle size (µm) | Amount of particles (%) |
|---|---|
| Over 355 | 0.0 |
| 300-355 | 16.3 |
| 250-300 | 72.4 |
| 212-250 | 11.0 |
| 150-212 | 0.3 |
| Under 150 | 0.0 |

2. Preparation of Sodium Sulfate Coated Enzyme Granules

Approximately 1,395 grams of the enzyme coated cores made above were reloaded into the coater and were subsequently coated with 861 grams of sodium sulfate which had been previously dissolved in water at 40° C. at a concentration of 20%. The coating parameters for spraying the salt cores were as follows:

| | |
|---|---|
| Enzyme Coated Core Charge | 1395 grams |
| Feed Rate: | 15-16 grams/minute |
| Atomization Pressure | 40 psi |
| Inlet Temperature | 90° C. |
| Outlet Temperature | 40-42° C. |
| Airflow: | 52-54 cfm |

The overall sodium sulfate layer mass yield and the mass yield of particles below and above 425 microns were as follows:

| | |
|---|---|
| Salt Layer Mass Yield: | 88.84% |
| <425 microns | 99.74% |
| >425 microns (overs) | 0.26% |

The particle size distribution is shown in Table 7.

TABLE 7

Particle Size Analysis for Enzyme Granules Produced in Example 7.2

| Particle size (µm) | Amount of particles (%) |
|---|---|
| Over 355 | 1.3 |
| 300-355 | 2.4 |
| 250-300 | 12.2 |
| 212-250 | 44.5 |
| 180-212 | 29.7 |
| Under 180 | 10.0 |

3. Preparation of PVA/Talc Coated Enzyme Granules

Approximately 1,395 grams of the enzyme coated cores made above were reloaded into the coater and were subsequently coated with 517 grams of a 10% solution of PVA (Erkomat), talc, and Neodol 23-6.5-T (Shell Chemical LP, Houston, Tex.) in water which had been previously prepared heated to 80° C. The solution included PVA, talc and neodol 23-6.5-T in a 30:65:5 solids ratio. The coating parameters were as follows:

| | |
|---|---|
| Enzyme Coated Core Charge | 1395 grams |
| Feed Rate | 9-11 grams/minute |
| Atomization Pressure | 46 psi |
| Inlet Temperature | 94° C. |
| Outlet Temperature | 52-57° C. |
| Airflow | 50 cfm |

The overall PVA layer mass yield and the mass yield of particles below and above 425 microns were as follows:

| | |
|---|---|
| PVA Layer Mass Yield: | 88.26% |
| >425 microns | 89% |
| >425 microns (overs) | 11% |

The particle size distribution is shown in Table 8.

TABLE 8

Particle Size Analysis for Enzyme Granules Produced in Example 7.3

| Particle size (µm) | Amount of particles (%) |
|---|---|
| Over 355 | 13.8 |
| 300-355 | 12.4 |
| 250-300 | 36.8 |
| 212-250 | 26.3 |
| 180-212 | 9.7 |
| Under 180 | 1.1 |

Example 8

Coatings on Small Granules to Reduce Dust

Small granules without protective coatings generate a significant amount of dust during pneumatic transport and filling operations, both in the enzyme granule manufacturing plant and at the customer's manufacturing plant. Dust can be both a hygienic problem and a manufacturing problem, so it must be minimized as much as possible. A small enzyme granule with the formulation listed below was manufactured at a 3,000 kg scale, and generated a significant amount of Heubach dust. The Heubach dust test is described, for example, in U.S. Pat. Nos. 5,324,649, 5,879,920, and 7,108,821, and in Becker et al. (1997) "Formulation of Detergent Enzymes" in *Enzymes in Detergency*, Van Ee, J. H., Misser, O., and Baasi, E., eds. Marcel Dekker, New York, pp. 299-325.

| Raw Material | Uncoated Granule |
|---|---|
| Sodium Sulfate Seed | 61.5% |
| Enzyme solids | 24.6% |
| Polyvinyl alcohol | 0.5% |
| Repel-o-tex SRP6 | 3.4% |
| Sodium Sulfate Layer | 10.0% |
| Total | 100.0% |

The Heubach dust level on the uncoated small granules shown above was 476 mg/pad and it is preferable to have granules with dust levels under 50 mg/pd for manufacturing.

Neodol Coating

A coating of 2% Neodol 23-6.5-T was sprayed onto the uncoated granules described above from a 10% aqueous solution using the following spray parameters in a fluid bed spray coater:

Neodol Spray Parameters

| Granule Charge | 1395 grams |
|---|---|
| Feed Rate | 15-16 grams/minute |
| Atomization Pressure | 40 psi |
| Inlet Temperature | 90° C. |
| Outlet Temperature | 40-42° C. |
| Airflow | 52-54 cfm |

The particle size distribution is shown in Table 9.

TABLE 9

Particle Size Analysis for Enzyme Granules Produced in Example 8 (Neodol Coating)

| Particle size (μm) | Amount of particles (%) |
|---|---|
| Over 355 | 0.0 |
| 300-355 | 21.6 |
| 250-300 | 68.0 |
| 212-250 | 9.6 |
| 150-212 | 0.5 |
| Under 150 | 0.3 |

In the Neodol coated granules, Heubach dust was significantly reduced to a value of 55 mg/pad.

HPMC/PEG Coating

An 8% coating of a mixture of 90% Methocel E-15 HPMC (hydroxypropyl methyl cellulose, Dow Corning) A-15 and 10% polyethylene glycol (PEG) 600 dissolved at a 5% solids level in water was sprayed onto uncoated granules using the spray parameters shown below:

| Granule Charge | 1395 grams |
|---|---|
| Feed Rate | 9-11 grams/minute |
| Atomization Pressure | 46 psi |
| Inlet Temperature | 94° C. |
| Outlet Temperature | 52-57° C. |
| Airflow | 50 cfm |

The particle size distribution is shown in Table 10.

TABLE 10

Particle Size Analysis for Enzyme Granule Produced in Example 8 (HPMC/PEG Coating)

| Particle size (μm) | Amount of particles (%) |
|---|---|
| Over 355 | 1.4 |
| 300-355 | 32.8 |
| 250-300 | 61.2 |
| 212-250 | 3.5 |
| 180-212 | 0.4 |
| Under 180 | 0.8 |

In the HPMC/PEG coated granules, Heubach dust was reduced to a level of 20 mg/pad.

Talc/PVA/Neodol Coating

A 10% coating of a mixture of 50% Talc, 40% PVA, and 10% Neodol 23-6.5-T dissolved in water at a 10% solids level was sprayed onto uncoated granules using the same spray parameters as described above for the HPMC/PEG coating. The particle size distribution is shown in Table 11.

TABLE 11

Particle Size Analysis for Enzyme Granules Produced in Example 8 (Talc/PVA/Neodol Coating)

| Particle size (μm) | Amount of particles (%) |
|---|---|
| Over 355 | 2.2 |
| 300-355 | 35.4 |
| 250-300 | 58.5 |
| 212-250 | 3.3 |
| 180-212 | 0.3 |
| Under 180 | 0.3 |

In the talc/PVA/Neodol coated granules, Heubach dust was reduced to a level of 16 mg/pad.

When this material was then coated with an additional 2% Neodol from a 10% solution using the spray parameters described above for the Neodol coating, the Heubach dust was further reduced to a level of 4 mg/pad.

Example 9

Enzyme-containing granules were prepared in a fluid bed spray coater with a barrier layer and an outer coating layer in a continuous process without removal of the granules from the coater between addition of coating layers.

152 kg of sodium sulfate crystals (from Hanhua Grade C), with a size range of 150 μm to 250 μm, was loaded into a pilot fluid bed coater and fluidized. 453 kg of neutral cellulase (19,295 U/g), 45 kg Repel-o-Tex 20% suspension, 7.1 kg sucrose, and 4.7 kg wheat starch was spray-coated onto the sodium sulfate crystals. 34 kg sodium sulfate solution (25% in water) was then sprayed onto the enzyme layer. An outer coating was then applied by spraying 33 kg of PVA:talc:Lutensol TO 65 (4:5:1, 25% solution in water).

The spray coating parameters were as follows:

Warm-up:

| | |
|---|---|
| Inlet air temperature | 68° C. |
| Fluidization air flow | 1125 Nm³/h |
| Atomization air pressure | 4.0 bar |

Enzyme Solution Spray Coating:

| | |
|---|---|
| Solution spray rate | 18.0 l/h for 20 minutes, then increased to 45 l/h over 450 minutes, then maintained at 42 l/h for remainder of run |
| Bed temperature | 48° C. |
| Fluidization air flow | 1125 Nm³/h over 420 minutes |
| Atomization air pressure | 4.0-5.5 bar, increased over 450 minutes |

Sulfate Solution Spray Coating:

| | |
|---|---|
| Solution spray rate | 36 l/h, then increased to 51 l/h over 30 minutes, then maintained at 51 l/h for remainder of run |
| Bed temperature | 50° C. |
| Fluidization air flow | 1170 Nm³/h |
| Atomization air pressure | 3.5-3.8 bar |

Outer Coating:

| | |
|---|---|
| Solution spray rate | 27 l/h, then decreased to 21 l/h over 75 minutes, then kept at 21 l/h for remainder of run |
| Bed temperature | 58° C. |
| Fluidization air flow | 1170 Nm³/h |
| Atomization air pressure | 5.5 bar |

197 kg of product was harvested through a 425 μm screen. The particle size distribution is shown in Table 12.

TABLE 12

Particle Size Analysis for Enzyme Granules Produced in Example 9

| Particle size (μm) | Amount of particles (%) |
|---|---|
| Over 355 | 0.7 |
| 300-355 | 15 |
| 250-300 | 59 |
| 212-250 | 24 |
| 180-212 | 1.8 |
| Under 150 | 0 |

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A method of making enzyme-containing granules, comprising
   a) coating an enzyme-containing layer onto cores in a fluidized bed spray coater,
   wherein at least 95% of said granules comprise a single core,
   wherein said cores consist of one or more inorganic salts,
   wherein said cores are pre-sieved to a particle dispersity index of 2.0 or less, and
   wherein at least 80% of said granules have a diameter of 150 to 355 microns,
   b) coating a layer comprising a barrier salt over said enzyme-containing layer, and
   c) coating a layer comprising polyvinyl alcohol over said barrier salt layer.

2. The method according to claim 1, wherein said cores consist of sodium sulfate.

3. The method according to claim 2, wherein at least 80% of said sodium sulfate cores have a diameter of 100 microns to 250 microns.

4. The method according to claim 3, wherein said sodium sulfate cores have a bulk density greater than 1.2 g/ml.

5. The method according to claim 1, wherein the granules are not removed from the fluidized bed spray coater prior to addition of the barrier salt layer.

6. The method according to claim 5, wherein said barrier salt layer comprises sodium sulfate.

7. The method according to claim 5, wherein the barrier salt layer comprises a mixture of two or more salts.

8. The method according to claim 7, wherein said mixture of two or more salts consists of sodium sulfate and magnesium sulfate.

9. The method according to claim 8, wherein said sodium sulfate and magnesium sulfate are present in said barrier salt layer at a ratio of 30:70 to 70:30 by weight of the barrier layer.

10. The method according to claim 5, wherein the granules are not removed from the fluidized bed spray coater prior to addition of the polyvinyl-alcohol-containing coating layer.

11. A method of making enzyme-containing granules, comprising
   a) coating an enzyme-containing layer onto cores in a fluidized bed spray coater,
   wherein at least 95% of said granules comprise a single core,
   wherein said cores consist of one or more inorganic salts,
   wherein said cores are pre-sieved to a particle dispersity index of 2.0 or less, and
   wherein at least 80% of said granules have a diameter of 150 to 355 microns,
   b) coating a layer comprising a barrier salt over said enzyme-containing layer, and
   c) coating a layer comprising a pigment over said barrier salt layer.

* * * * *